United States Patent

Akimoto et al.

[11] Patent Number: 5,962,740
[45] Date of Patent: Oct. 5, 1999

[54] PROCESSES FOR PRODUCING 4,6-BIS (SUBSTITUTED)PHENYLAZORESORCINOLS

[75] Inventors: Kazuhiko Akimoto; Kenichi Tokunaga; Isao Hashiba; Hideo Suzuki, all of Funabashi; Yasuo Katsumura, Osaka; Kazuo Osaki, Osaka; Hideo Kawashita, Osaka; Satoshi Yamazaki, Osaka, all of Japan

[73] Assignee: Nissan Chemical Industries, Ltd., Tokyo, Japan

[21] Appl. No.: 09/066,335

[22] PCT Filed: Oct. 31, 1996

[86] PCT No.: PCT/JP96/03199

§ 371 Date: Apr. 28, 1998

§ 102(e) Date: Apr. 28, 1998

[87] PCT Pub. No.: WO97/16411

PCT Pub. Date: May 9, 1997

[30] Foreign Application Priority Data

Nov. 2, 1995 [JP] Japan .................................. 7-309803
Dec. 12, 1995 [JP] Japan .................................. 7-346483

[51] Int. Cl.$^6$ .................................................. C07C 213/02
[52] U.S. Cl. ........................... 564/415; 534/688; 564/442; 564/443
[58] Field of Search ..................... 564/415, 442, 564/443; 534/688

[56] References Cited

U.S. PATENT DOCUMENTS 5,453,542  9/1995  Morgan et al. .

FOREIGN PATENT DOCUMENTS

A-61-501452  7/1986  Japan .
A-7-242604  9/1995  Japan .
WO 95/23130  8/1995  WIPO .

OTHER PUBLICATIONS

J. March, "Advanced Organic Chemistry", 4$^{th}$ John Wiley & Sons, p. 1224 (1992).

Primary Examiner—Samuel Barts
Attorney, Agent, or Firm—Oliff & Berridge, PLC

[57] ABSTRACT

A process for producing 4,6-bisphenylazoresorcinol of formula [2] wherein R represents halogen atom, $C_{1-5}$ alkyl group, hydroxycarbonyl or $C_{1-5}$ alkoxy group, n represents 0 or an integer of 1 to 5, and two or more Rs are the same or different from each other, which comprises reacting resorcinol with a benzenediazonium salt of formula [1] wherein R and n are the same as defined in the above formula [1], and X represents Cl, Br, $OSO_3H$ or $OPO_3H_2$, in an alkaline solvent, characterized in that (a) a solution of the compound of the formula [1] is mixed with a solution or suspension of an alkali metal or alkaline earth metal hydroxide to obtain an alkaline mixture, and this alkaline mixture is mixed to be reacted with a solution or suspension containing resorcinol and/or its alkali metal salt or alkaline earth metal salt, or (b) a solution of the compound of formula [1] is mixed to be reacted with a solution or suspension of a mixture of resorcinol with its alkali metal hydroxide or alkaline earth metal hydroxide 15 to 40 times by mol as much as the resorcinol. By the above-described method, the reaction volume can be reduced as compared with the conventional processes, and 4,6-bisphenylazoresorcinol can be obtained in high yield.

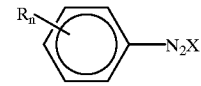

[1]

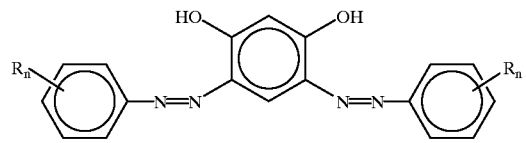

[2]

17 Claims, No Drawings

PROCESSES FOR PRODUCING 4,6-BIS (SUBSTITUTED)PHENYLAZORESORCINOLS

This application is a 371 of PCT/JP96/03199 filed Oct. 31, 1996.

TECHNICAL FIELD

The present invention relates to a process for producing 4,6-bis(substituted)phenylazoresorcinols, characterized in that a solution of a (substituted)-benzenediazonium salt is mixed with a solution or suspension of an alkali metal or alkaline earth metal hydroxide to thereby obtain an alkaline mixture, and that this alkaline mixture is then mixed to be reacted with resorcinol and/or its alkali metal salt or alkaline earth metal salt; or the (substituted)benzenediazonium salt and resorcinol are subjected to a coupling reaction in the presence of an alkali metal or alkaline earth metal hydroxide 15 to 40 times by mol as much as the resorcinol.

4,6-Diaminoresorcinol is easily obtained from 4,6-bis(substituted)phenylazoresorcinol by reduction thereof. (see: Advanced Organic Chemistry, 4th Edition, John Wiley and Sons, (1992) page 1224).

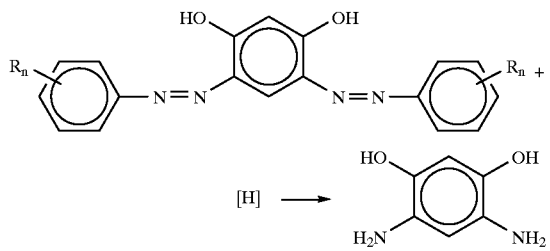

Since 4,6-diaminoresorcinol [DAR] becomes a polybenzbisoxazole (PBO) having various superior characteristics if it is condensed with terephthalic acid, it is important as a raw material thereof.

PBO is excellent in various points of strength, modulus of elasticity, heat resistance, chemical resistance and the like as compared with conventional superfibers, and development as ultra-superfibers is long expected Japanese Publication No. Sho 61-501452.

PRIOR ART

Hithertofore, some methods have been known as a process for producing 4,6-bisphenylazoresorcinols. As a process for obtaining 4,6-bisphenylazoresorcinol from resorcinol and benzenediazonium chloride by coupling reaction, Zollinger et al. obtain 4,6-bisphenylazoresorcinol in good yield under basic condition in a buffer solution [Helvetica Chimca Acta, XLI 1816–1823 (1958)].

However, this process using resorcinol as a raw material is advantageous in that DAR can be obtained in short steps, but a concentration of resorcinol is 0.1 wt %, and in view of practical use there is a problem on productivity.

Further, according to Japanese Patent Application Laid-open No. Hei 7-242604, 4,6-bis(substituted)phenylazoresorcinol is synthesized in relatively good yield by subjecting resorcinol and (substituted)benzenediazonium salt to a coupling reaction while controlling pH to 10 to 12.

However, even in this process, a dilute solution is used. This requires a large reaction volume, and it is difficult to practice the process industrially and economically.

If p-methoxybenzenediazonium chloride derived from p-methoxyaniline is used as a (substituted) benzenediazonium salt in place of chlorobenzenediazonium derived from aniline, concentration and yield are improved, but if the concentration exceeds 2 wt % in terms of resorcinol, the yield becomes very poor. It is difficult to industrially practice the same with such a concentration even though p-methoxyaniline which is more expensive as compared with aniline is used.

As mentioned above, conventional reactions obtain good yield only in dilute solution (concentration of resorcinols is 1 wt % or less) which is difficult to practice industrially and economically. An object of the present invention is to provide a process for producing 4,6-bis(substituted)phenylresorcinols in good yield in an industrially practicable concentration.

DISCLOSURE OF THE INVENTION

The present inventors have found that when a solution of a (substituted)benzenediazonium salt is made alkaline and is reacted with resorcinol and/or its alkali metal salt or alkaline earth metal salt, or the (substituted)-benzenediazonium salt and resorcinol are subjected to a coupling reaction in the presence of an alkali metal or alkaline earth metal hydroxide 15 to 40 times by mol as much as the resorcinol, 4,6-bis(substituted)phenylazoresorcinol can be obtained in good yield in an industrially practicable concentration.

That is, the process of the present invention is a process for producing 4,6-bis(substituted)phenylazoresorcinol of formula [2]

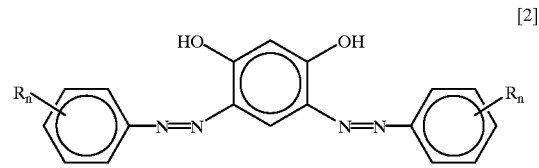

wherein R represents halogen atom, $C_{1-5}$ alkyl group, hydroxycarbonyl group or $C_{1-5}$ alkoxy group, n represents 0 or an integer of 1 to 5, and two or more Rs may be the same or different from each other, which comprises reacting, in an alkaline solvent, resorcinol with a (substituted) benzenediazonium salt of formula [1]

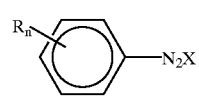

wherein R and n are the same as defined in the above formula [1], and X represents Cl, Br, $OSO_3H$ or $OPO_3H_2$, characterized in that (a) a solution of the (substituted)benzenediazonium salt of the formula [1] is mixed with a solution or suspension of an alkali metal or alkaline earth metal hydroxide to obtain an alkaline mixture, and this alkaline mixture is mixed to be reacted with a solution or suspension containing resorcinol and/or its alkali metal salt or alkaline earth metal salt, or (b) a solution of the (substituted)benzenediazonium salt is mixed to be reacted with a solution or suspension of a mixture of resorcinol with its alkali metal hydroxide or alkaline earth metal hydroxide 15 to 40 times by mol as much as the resorcinol.

The invention (a) of the present application relates to a process for producing 4,6-bis(substituted)

phenylazoresorcinol of the formula [2], characterized in that a solution of the (substituted)benzenediazonium salt of the formula [1] is mixed with a solution or suspension of an alkali metal or alkaline earth metal hydroxide to obtain an alkaline mixture, and this alkaline mixture is mixed to be reacted with a solution or suspension containing resorcinol and/or its alkali metal salt or alkaline earth metal salt.

The invention (b) of the present application relates to a process for producing 4,6-bis(substituted) phenylazoresorcinol salt, characterized in that a mixture of resorcinol with its alkali metal hydroxide or alkaline earth metal hydroxide 15 to 40 times by mol as much as the resorcinol is mixed to be reacted with a solution of a (substituted)benzenediazonium salt.

The present invention is described in more detail below.

The invention (a) of the present application is a process for producing 4,6-bis(substituted)phenylazoresorcinol by mixing a (substituted)benzenediazonium salt with a solution or suspension of an alkali metal or alkaline earth metal hydroxide to obtain an alkaline mixture, and then mixing this mixture with resorcinol and/or the alkali metal salt or alkaline earth metal salt, for example, sodium salt or calcium salt thereof. This method enables resorcinol to be high concentration of 2 to 10 wt % which has not conventionally be performed, and high yield and higher volume efficiency as compared with the conventional one have been achieved.

The production process of the invention (b) of the present application is an extremely simple production method by which 4,6-bis(substituted)phenylazoresorcinol can be obtained in a yield (resorcinol basis) of 70 to 80% by adding resorcinol, an alkali metal or alkaline earth metal hydroxide 15 to 40 times by mol as much as the resorcinol, and water, further adding dropwise a separately synthesized (substituted)-benzenediazonium salt twice times or more by mol as much as the resorcinol while stirring the resulting mixture, and reacting the resorcinol in a concentration of 2 to 10 wt % of the total amount of the reaction system. The reaction temperature may be higher than as expected in the reaction of this type. Therefore, there is no adverse influence even at 20° C., and reaction control is easy.

Reaction of the production process of the present invention proceeds with the following scheme.

difficult to increase yield of the 4,6-di-product. The yield is remarkably decreased in the case of particularly high concentration.

The present inventors have found that if the alkali metal or alkaline earth metal hydroxide in reaction system is used in a large amount, the yield is increased. This is assumed that if an alkali salt of mono-product is reacted, 4,6-di-product is produced, and if it is the free mono-product, 2,4-di-product is produced.

Further, if an alkali is used in large amount, a diazocoupling reaction proceeds slowly, so that a resorcin salt does not becomes free, and sequential reaction does not proceed. As a result, yield is not decreased even in a concentrated solution, making it possible to conduct industrial production under general conditions.

The mixture wherein a solution of the (substituted) benzenediazonium salt used in the invention (a) of the present application was made alkaline is obtained by, for example, preparing a mixture of anilines with an inorganic acid such as hydrochloric acid, sulfuric acid or phosphoric acid, adding a sodium nitrite aqueous solution to obtain a (substituted)benzenediazonium salt, and mixing a solution containing this (substituted)benzenediazonium salt with a solution or suspension of an alkali metal or alkaline earth metal hydroxide to thereby make the resulting mixture alkaline. Preferably, the solution containing the (substituted) benzenediazonium salt is added dropwise to the solution or suspension of the alkali metal or alkaline earth metal hydroxide, or the solution containing the (substituted) benzenediazonium salt and the solution or suspension containing the alkali metal or alkaline earth metal salt are mixed simultaneously, for example, on line.

More specifically, to a mixture of a (substituted) aniline of formula [3]:

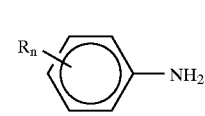

[3]

wherein R and n have the same meanings as defined in the formula [1], and water 5 to 10 times by weight as much as

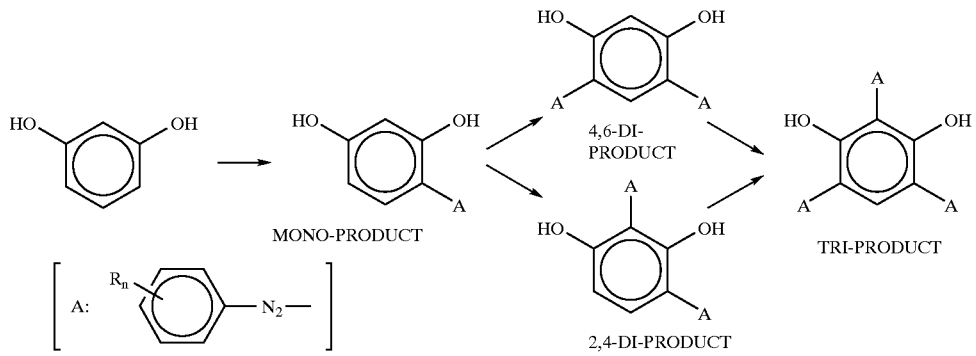

(definition of substituents in the scheme is the same as in the formula [1]).

Formation by a competing reaction of 2,4-bis(substituted) phenylazoresorcinol (hereinafter, referred to as 2,4-di-product) which is an isomer and formation by a sequential reaction of mono-product and tri-product decrease yield of 4,6-bis(substituted)phenylazoresorcinol (hereinafter, referred to as 4,6-di-product), and it is a reaction which is the (substituted)aniline is added dropwise under cooling an inorganic acid 2.5 to 10 times by equivalent as much as the (substituted)aniline, and to this mixture is added dropwise under temperature below 10° C. an alkali nitrite, such as sodium nitrite or potassium nitrite, 1 to 1.5 times by equivalent as much as the (substituted)aniline dissolved into water 2 to 3 times by weight as much as the (substituted)aniline, to thereby obtain a (substituted)benzenediazonium salt. At least one of inorganic acids selected from hydrochloric acid, hydrobromic acid, sulfuric acid and phosphoric acid is used as the inorganic acid. Of those inorganic acids, hydrochloric acid is preferred industrially and economically. Specific examples of the (substituted)aniline used in this reaction include aniline, 2-chloroaniline, 4-chloroaniline, 2,6-dichloroaniline, o-toluidine, m-toluidine, p-toluidine, anthranilic acid, o-anisidine, m-anisidine and p-anisidine. Considering economical standpoint, stability of compound, and the like, aniline is most preferred.

After formation of a diazonium salt, nitrous acid formed by sodium nitrite used in excess may be treated with urea or sulfamic acid. By this treatment, decomposition of the diazonium salt is suppressed.

A solution of the (substituted)benzenediazonium salt thus obtained is mixed with a solution or suspension of an alkali metal or alkaline earth metal hydroxide to make the resulting mixture alkaline.

Examples of the alkali metal or alkaline earth metal hydroxide used in this reaction are NaOH, KOH, LiOH, $Ca(OH)_2$, $Mg(OH)_2$, $Ba(OH)_2$, and the like. From the economical standpoint, NaOH and KOH are preferred.

The amount of the alkali metal or alkaline earth metal hydroxide is in the range of 1.1 to 20 times by equivalent, and preferably 1.5 to 10 times by equivalent, as much as the (substituted)benzenediazonium salt, as an excess amount for neutralizing acids in the (substituted)benzenediazonium salt solution and further making the same alkaline. If the excess amount of the alkali metal or alkaline earth metal hydroxide is less than 1.1 times by equivalent, yield of the objective 4,6-di-product is not improved. Even if the excess amount of the alkali metal or alkaline earth metal hydroxide is increased so as to exceed 20 times by equivalent, the effect by the increase of the alkali metal or alkaline earth metal hydroxide is not exhibited.

The temperature in mixing and reacting the (substituted) benzenediazonium salt with the alkali metal or alkaline earth metal hydroxide is −50 to 50° C., and preferably −50 to 15° C. Where a solvent is only water, solidification occurs. Therefore, the temperature of −5 to 10° C. is preferred. Because, within the range of −50 to 10° C., the (substituted) benzenediazonium salt as the raw material and a reaction intermediate formed (it is assumed to be (substituted) benzenediazonium hydroxide) can be present in a stable state. It is difficult to decrease a temperature to lower than −50° C., and at a temperature exceeding 15° C. the reaction intermediate can not be present in a stable state.

Mixing the solution of the (substituted)benzenediazonium salt with the solution or suspension of the alkali metal or alkaline earth metal hydroxide is generally conducted in a reaction vessel. In some cases, the reaction vessel may function as a storage tank of the mixture. However, this mixing may be conducted in the line connecting to a reaction vessel in which a reaction of the resulting mixture with resorcinol and/or its alkali metal salt or alkaline earth metal salt is conducted. By this, the number of reactors can be decreased. Further, the time of change with the passage of time of the reaction intermediate formed can be shortened.

The thus-obtained mixture of the solution of the (substituted)benzenediazonium salt with the solution or suspension of the alkali metal or alkaline earth metal hydroxide is mixed with resorcinol and/or the alkali metal salt or alkaline earth metal salt, and a coupling reaction is conducted to obtain the objective product. In general, the mixture is added under stirring, for example, added dropwise, flown down or poured, to the solution of the resorcinol and/or its alkali metal salt or alkaline earth metal salt. The stirring makes it possible to avoid locally excessive progress of reaction, so that formation of tri-product can be minimized.

Examples of salt of resorcinol which can be used are salts of alkali metal such as sodium or potassium, and salts of alkaline earth metal such as magnesium or barium. Since the mixture of the (substituted)benzenediazonium salt and an alkali is alkaline, the amount of the alkali metal or alkaline earth metal hydroxide used for the production of the salt of resorcinol is 0 to 20 times by equivalent, and preferably 0 to 5 times by equivalent, in view of the fact that use of only resorcinol forms a salt in the reaction system. Where the excess amount of the hydroxide in the mixture of the (substituted)benzenediazonium salt with the hydroxide is 5 to 20 times by equivalent as much as the (substituted) benzenediazonium salt, the mixture of the (substituted) benzenediazonium salt with the alkali metal or alkaline earth metal hydroxide is generally reacted with only resorcinol.

The amount of the (substituted)benzenediazonium salt in mixing the mixture of the (substituted)benzenediazonium salt and an alkali metal or alkaline earth metal hydroxide, and resorcinol or the alkali metal salt or alkaline earth metal salt is preferably 2 times or more by mol as much as the total amount of resorcinol and/or the salt from the standpoint of yield of the objective product. However, if the amount is too large, tri-product is formed. Therefore, the amount is preferably 2.05 to 2.20 times by mol. If the amount is less than 2.05 times by mol, resorcinol and/or mono-product tend to remain, and if the amount is more than 2.20 times by mol, tri-product tends to form.

Water or an organic solvent which is uniformly mixed with water can be used as a solvent in mixing the solution of the (substituted)benzenediazonium salt with an alkali metal or alkaline earth metal hydroxide, and in reacting resorcinol and/or its alkali metal salt or alkaline earth metal salt with the mixture of the (substituted)benzenediazonium salt and the hydroxide. Examples of the organic solvent which can be used include methanol, ethanol, propanol, t-butanol, dioxane, tetrahydrofuran, acetone, dimethylformamide (DMF), dimethylsulfoxide (DMSO) and dimethylimidazolidinone (DMI). However, DMF, DMSO and acetone which are unstable to strong alkali are not preferred. The most preferred solvent is water, because post-treatment operation is easy due to unnecessity of recovery of organic solvent, and yield is most high.

The reaction with resorcinol and/or resorcinol alkali salt is relatively fast, but the time required for reaction depends on a reaction temperature. The reaction temperature is generally −50 to 50° C. The reaction rate increases as the reaction temperature elevates. In order to avoid decomposition of the reaction intermediate (it is assumed to be a (substituted)benzenediazonium hydroxide) of the raw material and a di-product formed, a temperature of −50 to +20° C. is preferred. If the solvent is only water, solidification occurs. Therefore, a temperature of −5 to +20° C. is preferred. The reaction time is generally 0.1 to 10 hours at −5 to +20° C.

In order to avoid decomposition of 4,6-di-product in an alkali solution, it is preferred to immediately conduct post-treatment after completion of the reaction.

Next, the invention (b) of the present application is explained.

Examples of the alkali metal or alkaline earth metal hydroxide used in this reaction are NaOH, KOH, $Ca(OH)_2$, $Mg(OH)_2$, $Ba(OH)_2$, LiOH and the like. NaOH and KOH are preferred. The amount of the alkali metal or alkaline earth metal hydroxide is 15 to 40 times by mol, and preferably 15 to 20 times by mol, as much as the resorcinol. If the amount is more than 20 times by mol, the effect obtained is not improved so much and is unchanged.

The reaction temperature is in the range of −50 to +50° C. Slight. improvement in yield is recognized at low temperature, but there is the problem on cost for reinforement of cooling facilities. Slight decrease in yield is observed at a temperature higher than 30° C. Therefore, the preferred reaction temperature is −10 to +20° C. In the initial stage of reaction, if the amount of alkali hydroxide is large at low temperature, a slurry of the mixture containing an alkali salt of resorcinol has high viscosity, making it difficult to stir. Therefore, it is also effective that the diazonium salt is added by, for example, dropwise addition, flowing down or pouring, to the mixture containing an alkali salt of resorcinol in an amount of 0.1 to 1.3 times by mol as much as the resorcinol at 20 to 50° C., at the time that a slurry viscosity is decreased, the temperature is adjusted to −10 to 20° C., and the diazonium salt is further added by dropwise addition, flowing down or pouring to conduct reaction.

This is also effective from the standpoint of sequential reaction in that the 4,6-di-product precipitates as a solid, and is removed outside the reaction system.

Water or a mixed solvent of water and an organic solvent which is uniformly compatible with water can be used as the reaction solvent. Examples of the organic solvent which can be used are methanol, ethanol, propanol, t-butanol, dioxane, tetrahydrofuran, acetone, dimethylformamide (DMF), dimethylsulfoxide (DMSO), dimethylimidazolidinone (DMI) and the like. DMF, DMSO and acetone which are caused to be decomposed by strong alkaline are not preferred. Water is most preferred, and gives best results in economical point, ease of post-treatment and yield.

The (substituted)benzenediazonium salt used in the present invention is obtained as follows.

To a mixture of the (substituted)aniline of the formula [3] and water 5 to 10 times by weight is added dropwise an inorganic acid 2.5 to 4 equivalents to the aniline under cooling, and to the resulting mixture is added dropwise sodium nitrite or potassium nitrite 1 to 1.5 times by mol as much as the (substituted)aniline, dissolved in water 2 to 3 times by weight at 10° C. or less, to thereby obtain a (substituted)benzenediazonium salt. The inorganic acid used is at least one inorganic acid selected from hydrochloric acid, hydrobromic acid, sulfuric acid and phosphoric acid. Of those inorganic acids, hydrochloric acid is preferred economically and industrially.

Specific examples of the aniline include aniline, 2-chloroaniline, 4-chloroaniline, 2,6-dichloroaniline, o-toluidine, m-toluidine, p-toluidine, anthranilic acid, o-anisidine, m-anisidine and p-anisidine. It is preferable to use either of those anilines. Aniline is most preferred from economical point, stability of compound, and the like.

After formation of the diazonium salt, nitrous acid formed by sodium nitrite used in excess may be treated with urea or sulfamic acid and used. This treatment suppresses decomposition of the diazonium salt.

The substituted benzenediazonium salt thus obtained is added dropwise, in an amount of 2 or more by mol as much as the resorcinol, to and reacted with a mixture of resorcinol, an alkali hydroxide 15 to 40 times by mol as much as the resorcinol and water which are stirred. In this reaction system, the concentration of resorcinol is preferably 2–10 wt %. It is preferable for the diazonium salt to be used in an amount 2 times or more by mol as much as the resorcinol in the yield of the objective product. However, if it is used too much, a tri-form is formed. Therefore, the amount is preferably 2.05 to 2.20 times by mol.

The reaction is relatively fast, and at 0° C. the reaction is completed in about 2 hours after adding the diazonium salt. It is preferable that the 4,6-di-product is immediately subjected to post-treatment after completion of the reaction in order to avoid decomposition in the alkali solution.

The post-treatment after completion of the reaction is that the reaction liquid is filtered, whereby almost all of the tri-form is removed. If the amount of water in the reaction is small, 4,6-di-product is also separated as a solid. Therefore, it is necessary to dissolve and recover the 4,6-di-product by washing the solid with water. If the filtrate and washing liquid made acidic with hydrochloric acid, acetic acid, sulfuric acid, phosphoric acid, or the like, 4-monoproduct, 4,6-di-product and 2,4-di-product are precipitated. Those are collected by filtration, dried and then subjected to reduction step. Where it is necessary to separate 4-mono product, if the solid obtained is washed with $Na_2 CO_3$ aqueous solution, only 4-mono-product is dissolved and can be removed.

Reduction of the 4,6-di-product is conducted using a metal catalyst such as Pd-C. In this case, reduction is conducted with hydrogen at atmospheric pressure or under pressure using an aqueous medium or a mixed solvent of an alcohol and water to which a slight amount of lower alcohol is added, and adding hydrochloric acid 3 to 5 times by mol as much as the 4,6-di-product, and a catalyst.

After the reduction, when the catalyst is filtered off and a large amount of hydrochloric acid is added to the filtrate, 4,6-diaminoresorcinol hydrochloride is precipitated. By collecting the precipitate by filtration, 4,6-diaminoresorcinol hydrochloride can be obtained. When the filtrate is made alkaline by shielding oxygen, aniline is separated as an oil layer. Therefore, the aniline can be recovered for reuse.

The preferred embodiments of the production process of the invention (a) of the present invention are successively described below.

(1) A method wherein a solvent for the solution of the (substituted)benzenediazonium salt and its alkali metal or alkaline earth metal hydroxide is water. If the solvent is water, reaction yield and volume efficiency both are high, and recovery of organic solvent, which is an additional operation, is not necessary. Thus, the post-treatment is easy.

(2) A method of practical embodiment of the invention (a) or the above (1), wherein the amount of the hydroxide in mixing the solution of the (substituted)benzenediazonium salt with the solution or suspension of the alkali metal or alkaline earth metal hydroxide is such that the excess amount after neutralizing acid in the solution of the (substituted)benzenediazonium salt is 1.1 to 20 times by equivalent, and preferably 1.5 to 10 times by equivalent, as much as the (substituted)benzenediazonium salt. As described above, solubility of resorcinol is increased, and stability of the (substituted)benzenediazonium salt present and 4,6-di-product formed are also increased.

(3) A method of practical embodiment of the invention (a) or the above (1) or (2), wherein the amount of the (substituted)benzenediazonium salt in mixing the mixture of the (substituted)benzenediazonium salt and its alkali metal or alkaline earth metal hydroxide, with resorcinol or the alkali metal salt or alkaline earth metal salt is 2.05 to 2.20 times by mol as much as the total amount of the resorcinol and/or its salt. If the amount is less than 2.05 times by mol, resorcinol and/or mono-product tend to remain, and if it exceeds 2.20 times by mol, tri-product tends to form.

(4) A method of practical embodiment of the invention (a) or the above (1), (2) and (3), wherein the (substituted) benzenediazonium salt is a benzenediazonium salt. The benzenediazonium salt is most industrial and economical.

9

(5) A method of the invention (a) or the above (1), (2), (3) and (4), wherein the alkali metal hydroxide is sodium hydroxide. Sodium hydroxide is economical and is easy to handle.

(6) The operation of mixing the (substituted) benzenediazonium salt with the alkali metal or alkaline earth metal hydroxide to thereby make the same alkaline can be conducted in a connecting line to a reaction vessel which conducts reaction of the mixture with resorcinol and/or the alkali metal salt or alkaline earth metal salt. This can decrease the number of reaction vessel and/or storage tank of the mixture.

(7) A method of practical embodiment of the invention (a) or the above (1) to (6), wherein mixing an alkaline mixture of the (substituted)benzenediazonium salt with a solution or suspension containing resorcinol and/or its alkali metal salt or alkaline earth metal salt is addition, for example, dropwise addition, flowing down or pouring, of the alkaline mixture of the (substituted)benzenediazonium salt to the solution or suspension containing resorcinol and/or its alkali metal salt or alkaline earth metal salt.

This method can avoid localization of the (substituted) benzenediazonium salt, and therefore can decrease formation of tri-product.

The preferred practical embodiments of the production process of the invention (b) of the present application are successively described.

Production process of reacting a solution of the (substituted)benzenediazonium salt with a solution or suspension of a mixture of resorcinol and its alkali metal hydroxide or alkaline earth metal hydroxide 15 to 40 times by mol as much as the resorcinol:

Localization of the (substituted)benzenediazonium salt can be avoided, and formation ratio of 2,4-di-product and tri-product is decreased.

Production process wherein the solvent is water or a mixture of water and a water-soluble organic solvent, and the amount of resorcinol used is 2 to 10 wt % of the total amount of the reaction system:

When the solvent is water, post-treatment is easy, and yield is the highest one. Further, if the amount of resorcinol used is 2 to 10 wt % of the total amount of the reaction system, the objective compound can be obtained in the yield of 70 to 80%.

Production process of the invention (b) wherein the (substituted)benzenediazonium chloride is benzenediazonium chloride and production process of the above embodiment:

The objective compound obtained in the case of using the benzenediazonium chloride is most preferable as compared with other (substituted)benzenediazonium.

Production process of the invention (b) wherein the reaction solvent is water and production process of either of the above embodiments.

Production process of the invention (b) wherein the hydroxide is sodium hydroxide or potassium hydroxide and production process of either of the above embodiments.

Production process of the invention (b) wherein addition of a solution of the (substituted)benzenediazonium salt is dropwise addition, flowing down or pouring of the (substituted)benzenediazonium salt and production process of either of the above embodiments.

BEST MODE FOR CARRYING OUT THE INVENTION

The invention is described below in more detail by the examples, but the invention is not limited thereto in any way.

10

Examples 1 to 4 and Comparative Example 1 relate to the invention (a) of the present application, and Examples 5 to 8 and Comparative Example 2 relate to the invention (b) of the present application.

(Invention (a) of the Present Application)

EXAMPLE 1

A solution of 3.04 g of sodium nitrite dissolved in 5.5 g of water at 0 to 5° C. was added dropwise to a mixture of 4.1 g of aniline, 9.8 g of 35% hydrochloric acid and 10 g of water to synthesize a benzenediazonium chloride aqueous solution. This benzenediazonium chloride aqueous solution and a solution composed of 4.9 g of NaOH and 12.3 g of water were sent by pump in the same molar ratio, and were mixed in line while cooling at 10° C. The resulting mixture was added dropwise to a mixture composed of 2.2 g of resorcinol, 2.4 g of NaOH and 11 g of water at 10° C. over 40 minutes. After completion of the dropwise addition, the resulting mixture was stirred at 10° C. for 3 hours.

Hydrochloric acid was added to the reaction mixture to make the same acidic. Solid precipitated was collected by filtration, washed with water and dried to obtain a dark red solid. As a result of determination with a liquid chromatography, the amount of 4,6-di-product was 5.8 g and the yield was 91%.

EXAMPLE 2

A solution of 3.04 g of sodium nitrite dissolved in 5.5 g of water at 0 to 5° C. was added dropwise to a mixed solution of 4.1 g of aniline, 9.8 g of 35% hydrochloric acid and 10 g of water to synthesize a benzenediazonium chloride aqueous solution.

This benzenediazonium chloride aqueous solution was added dropwise to a solution composed of 5.5 g of NaOH and 13.8 g of water at 10° C. or less to prepare a mixed solution.

This mixed solution was added dropwise to a mixture composed of 2.2 g of resorcinol, 2.4 g of NaOH and 11 g of water at 10° C. over 40 minutes. After completion of the dropwise addition, the resulting mixture was stirred at 10° C. for 3 hours. After completion of the reaction, hydrochloric acid was added to the reaction mixture to make the same acidic. Solid precipitated was collected by filtration, washed with water and dried to obtain a dark red solid. As a result of determination with a liquid chromatography, the amount of 4,6-di-product was 5.6 g and the yield was 88%.

EXAMPLE 3

A solution of 3.04 g of sodium nitrite dissolved in 5.5 g of water at 0 to 5° C. was added dropwise to a mixed solution of 4.1 g of aniline, 9.8 g of 35% hydrochloric acid and 10 g of water to synthesize a benzenediazonium chloride aqueous solution. This benzenediazonium chloride aqueous solution was added dropwise to a solution composed of 5.5 g of NaOH and 13.8 g of water at 10° C. or less to prepare a mixed solution.

This mixed solution was added dropwise to a mixture composed of 2.2 g of resorcinol and 11 g of water at 10° C. over 40 minutes. After completion of the dropwise addition, the resulting mixture was stirred at 10° C. for 3 hours. After completion of the reaction, hydrochloric acid was added to the reaction mixture to make the same acidic. Solid precipitated was collected by filtration, washed with water and dried to obtain a dark red solid. As a result of determination with a liquid chromatography, the amount of 4,6-di-product was 5.8 g and the yield was 91%.

EXAMPLE 4

A solution of 3.04 g of sodium nitrite dissolved in 5.5 g of water at 0 to 5° C. was added dropwise to a mixed solution of 4.1 g of aniline, 9.8 g of 35% hydrochloric acid and 5 g of water to synthesize a benzenediazonium chloride aqueous solution.

This benzenediazonium chloride aqueous solution was added dropwise to a solution composed of 5.5 g of NaOH and 13.8 g of water at 10° C. or less to prepare a mixed solution.

This mixed solution was added dropwise to a mixture composed of 2.2 g of resorcinol and 5 g of water at 10° C. over 40 minutes. After completion of the dropwise addition, the resulting mixture was stirred at 10° C. for 3 hours. After completion of the reaction, hydrochloric acid was added to the reaction mixture to make the same acidic. Solid precipitated was collected by filtration, washed with water and dried to obtain a dark red solid. As a result of determination with a liquid chromatography, the amount of 4,6-di-product was 5.7 g and the yield was 90%.

Comparative Example 1

A solution of 2.76 g of sodium nitrite dissolved in 5.5 g of water at 0 to 5° C. was added dropwise to a mixed solution of 3.76 g of aniline, 9.4 g of 35% hydrochloric acid and 10 g of water to synthesize a benzenediazonium chloride aqueous solution.

2.2 g of resorcinol, 8 g of NaOH and 22 g of water were charged and well stirred at 10° C., and the above benzenediazonium chloride aqueous solution separately synthesized was added dropwise to the resulting mixture while maintaining at 10° C. over 30 minutes. After completion of the dropwise addition, the resulting mixture was stirred at 10° C. for 2 hours. Insoluble matters were filtered, and the insoluble matters collected by filtration were washed with 30 g of water. The filtrate and washing liquid were combined, and the resulting liquid was made acidic with hydrochloric acid. Solid precipitated was collected by filtration washed with water, and dried to obtain a dark red solid. As a result of determination with a liquid chromatography, the amount of 4,6-di-product was 2.22 g, and the yield was 35%.

(Invention (b) of the Present Application)

EXAMPLE 5

<Synthesis of Benzenediazonium Chloride Aqueous Solution>

A solution of 2.76 g of sodium nitrite dissolved in 5.5 g of water at 0 to 5° C. was added dropwise to a mixed solution of 3.76 g of aniline, 9.4 g of 35% hydrochloric acid and 10 g of water to synthesize a benzenediazonium chloride aqueous solution.

<Synthesis of 4,6-Bisphenylazoresorcinol>

2.2 g (0.02 mol) of resorcinol, 16 g (0.4 mol) of NaOH and 22 g of water were charged and well stirred at 10° C., and the entire amount (the diazonium salt is 2.0 times by mol as much as the resorcinol) of the above benzenediazonium chloride aqueous solution separately synthesized was added dropwise to the resulting mixture while maintaining the reaction temperature at 10° C. over 30 minutes. After completion of the dropwise addition, the resulting mixture was stirred at 10° C. for 2 hours. Insoluble matters were filtered, and the insoluble matters collected by filtration were washed with 30 g of water. The filtrate and washing liquid were combined, and the resulting liquid was made acidic with hydrochloric acid. Solid precipitated was collected by filtration, washed with water, and dried to obtain a dark red solid. As a result of determination with a liquid chromatography, the amount of 4,6-di-product was 4.64 g, and the yield was 73%.

EXAMPLE 6

<Synthesis of Benzenediazonium Chloride Aqueous Solution>

A solution of 2.76 g of sodium nitrite dissolved in 5.5 g of water at 0 to 5° C. was added dropwise to a mixed solution of 3.95 g of aniline, 9.4 g of 35% hydrochloric acid and 10 g of water to synthesize a benzenediazonium chloride aqueous solution.

<Synthesis of 4,6-Bisphenylazoresorcinol>

2.2 g (0.02 mol) of resorcinol, 16 g (0.4 mol) of NaOH and 22 g of water were charged and well stirred at 10° C., and the entire amount (the diazonium salt is 2.1 times by mol as much as the resorcinol) of the above benzenediazonium chloride aqueous solution separately synthesized was added dropwise to the resulting mixture while maintaining the reaction temperature at 10° C. over 30 minutes. After completion of the dropwise addition, the resulting mixture was stirred at 10° C. for 2 hours. Insoluble matters were filtered, and the insoluble matters collected by filtration were washed with 30 g of water. The filtrate and washing liquid were combined, and the resulting liquid was made acidic with hydrochloric acid. Solid precipitated was collected by filtration, washed with water, and dried to obtain a dark red solid. As a result of determination with a liquid chromatography, the amount of 4,6-di-product was 4.96 g, and the yield was 78%.

EXAMPLE 7

<Synthesis of Benzenediazonium Chloride Aqueous Solution>

A solution of 2.76 g of sodium nitrite dissolved in 5.5 g of water at 0 to 5° C. was added dropwise to a mixed solution of 3.76 g of aniline, 9.4 g of 35% hydrochloric acid and 10 g of water to synthesize a benzenediazonium chloride aqueous solution.

<Synthesis of 4,6-Bisphenylazoresorcinol>

2.2 g (0.02 mol) of resorcinol, 16 g (0.4 mol) of NaOH and 22 g of methanol were charged and well stirred at 10° C. and the entire amount (the diazonium salt is 2.1 times by mol as much as the resorcinol) of the above benzenediazonium chloride aqueous solution separately synthesized was added dropwise to the resulting mixture while maintaining the reaction temperature at 10° C. over 30 minutes. After completion of the dropwise addition, the resulting mixture was stirred at 10° C. for 2 hours. Methanol was distilled off under reduced pressure, and 30 g of water was added. Insoluble matters were filtered, and the insoluble matters collected by filtration were washed with 30 g of water. The filtrate and washing liquid were combined, and the resulting liquid was made acidic with hydrochloric acid. Solid precipitated was collected by filtration, washed with water, and dried to obtain a dark red solid. As a result of determination with a liquid chromatography, the amount of 4,6-di-product was 4.1 g, and the yield was 65%.

EXAMPLE 8

<Synthesis of Benzenediazonium Chloride Aqueous Solution>

A solution of 2.76 g of sodium nitrite dissolved in 5.5 g of water at 0 to 5° C. was added dropwise to a mixed solution of 3.76 g of aniline, 9.4 g of 35% hydrochloric acid and 10 g of water to synthesize a benzenediazonium chloride aqueous solution.

<Synthesis of 4,6-Bisphenylazoresorcinol>

2.2 g (0.02 mol) of resorcinol, 24 g (0.6 mol) of NaOH and 22 g of water were charged and well stirred at 10° C., and the entire amount (the diazonium salt is 2.1 times by mol as much as the resorcinol) of the above benzenediazonium chloride aqueous solution separately synthesized was added dropwise to the resulting mixture while maintaining the reaction temperature at 10° C. over 30 minutes. After completion of the dropwise addition, the resulting mixture was stirred at 10° C. for 2 hours. Methanol was distilled off under reduced pressure, and 30 g of water was added. Insoluble matters were filtered, and the insoluble matters collected by filtration were washed with 30 g of water. The filtrate and washing liquid were combined, and the resulting liquid was made acidic with hydrochloric acid. Solid precipitated was collected by filtration, washed with water, and dried to obtain a dark red solid. As a result of determination with a liquid chromatography, the amount of 4,6-di-product was 4.7 g, and the yield was 74%.

Comparative Example 2

<Synthesis of Benzenediazonium Chloride Aqueous Solution>

A solution of 2.76 g of sodium nitrite dissolved in 5.5 g of water at 0 to 5° C. was added dropwise to a mixed solution of 3.76 g of aniline, 9.4 g of 35% hydrochloric acid and 10 g of water to synthesize a benzenediazonium chloride aqueous solution.

<Synthesis of 4,6-Bisphenylazoresorcinol>

2.2 g (0.02 mol) of resorcinol, 8 g (0.2 mol) of NaOH and 22 g of water were charged and well stirred at 10° C., and the entire amount (the diazonium salt is 2.0 times by mol as much as the resorcinol) of the above benzenediazonium chloride aqueous solution separately synthesized was added dropwise to the resulting mixture while maintaining the reaction temperature at 10° C. over 30 minutes. After completion of the dropwise addition, the resulting mixture was stirred at 10° C. for 2 hours. Insoluble matters were filtered, and the insoluble matters collected by filtration were washed with 30 g of water. The filtrate and washing liquid were combined, and the resulting liquid was made acidic with hydrochloric acid, washed with water, and dried to obtain a dark red solid. Solid precipitated was collected by filtration. As a result of determination with a liquid chromatography, the amount of 4,6-di-product was 2.22 g, and the yield was 35%.

Comparing Examples 5 to 8 with Comparative Example 2, the examples were that the molar ratio of alkali to resorcinol was 20 times or 30 times, and the yield of 4,6-di-product was 65 to 74%. Contrary to this, the comparative example was that the molar ratio of alkali was 10 times, and the yield was as low as 35%.

Thus, the yield was markedly improved by increasing the molar ratio of alkali from 10 times to 20 to 30 times. such a remarkable yield improvement effect by making the molar ratio of alkali from "in excess" to "further in excess" is more than expected one.

Utilization Possibility on Industry (Invention (a) of the Present Application)

By mixing a solution of a (substituted)benzenediazonium salt with a solution or suspension of an alkali metal or alkaline earth metal hydroxide to thereby obtain an alkaline mixture, and reacting this alkaline mixture with a solution or suspension of resorcinol and/or the alkali metal salt or alkaline earth metal salt, high yield of 4,6-bis(substituted) phenylazoresorcinol could be maintained without lowering the concentration of resorcinol. This made possible to decrease the reaction volume to about 1/5 to 1/15 the conventional one (in short, the volume increased to 5 to 15 times).

(Invention (b) of the Present Application)

By adding dropwise, flowing down, or pouring a solution of a (substituted)benzenediazonium salt to a solution or suspension of a mixture of resorcinol with an alkali metal hydroxide or alkaline earth metal hydroxide 15 to 40 times by mol as much as the resorcinol, high yield of 4,6-bis (substituted)phenylazoresorcinol could be maintained without lowering the concentration of resorcinol.

This made possible to decrease the reaction volume to about 1/5 to 1/15 the conventional one (in short, the volume efficiency is increased to 5 to 15 times).

We claim:

1. A process for producing 4,6-bis(substituted)phenylazoresorcinol of formula [2]

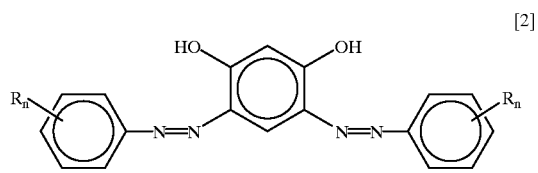

[2]

wherein R represents halogen atom, $C_{1-5}$ alkyl group, hydroxycarbonyl group or $C_{1-5}$ alkoxy group, n represents 0 or an integer of 1 to 5, and two or more Rs may be the same or different from each other, which comprises reacting, in an alkaline solvent, resorcinol with a (substituted) benzenediazonium salt of formula [1]

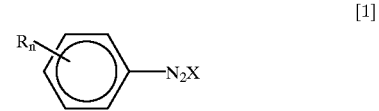

[1]

wherein R and n are the same as defined in the above formula [1], and X represents Cl, Br, $OSO_3H$ or $OPO_3H_2$, characterized in that (a) a solution of the (substituted)benzenediazonium salt of formula [1] is mixed with a solution or suspension of an alkali metal or alkaline earth metal hydroxide to obtain an alkaline mixture, and this alkaline mixture is then mixed to be reacted with a solution or suspension containing resorcinol and/or its alkali metal salt or alkaline earth metal salt, or (b) a resorcinol is reacted with the (substituted) benzenediazonium salt in the presence of an alkali metal hydroxide or alkaline earth metal hydroxide 15 to 40 times by mol as much as the resorcinol.

2. The production process as claimed in claim 1, characterized in that a solution of the (substituted) benzenediazonium salt of the formula [1] is mixed with a solution or suspension of an alkali metal or alkaline earth metal hydroxide to obtain an alkaline mixture, and this alkaline mixture is mixed to be reacted with a solution or suspension containing resorcinol and/or its alkali metal salt or alkaline earth metal salt.

3. The production process as claimed in claim 2, wherein a solvent for the solution of the (substituted) benzenediazonium salt and the solution or suspension of the alkali metal or alkaline earth metal hydroxide is water.

4. The production process as claimed in claim 2, wherein an amount of the hydroxide in mixing the solution of the (substituted)benzenediazonium salt with the solution or suspension of the alkali metal or alkaline earth metal hydroxide is 1.1 to 20 times by equivalent as much as the (substituted)

benzenediazonium salt, as an excess amount for further alkalize the (substituted)benzenediazonium salt solution after neutralizing an acid in the (substituted) benzenediazonium salt solution.

5. The production process as claimed in claim 2, wherein an amount of the (substituted)diazonium salt in mixing the alkaline mixture of the (substituted)benzenediazonium salt and the alkali metal or alkaline earth metal hydroxide with the solution or suspension of resorcinol or its alkali metal salt or alkaline earth metal salt is 2.05 to 2.20 times by mol as much as the total amount of the resorcinol and/or its alkali metal salt or alkaline earth metal salt.

6. The production process as claimed in claim 2, wherein the (substituted)benzenediazonium salt is a benzenediazonium salt.

7. The production process as claimed in claim 2, wherein the hydroxide is sodium hydroxide.

8. The production process as claimed in claim 2, wherein mixing the solution of the (substituted)benzenediazonium salt with the solution or suspension of the alkali metal or alkaline earth metal hydroxide is conducted in a line to a reaction vessel in which reaction of the mixture with the resorcinol and/or the alkali metal salt or alkaline earth metal salt is conducted.

9. The production process as claimed in claim 2, wherein mixing the alkaline mixture of the (substituted) bezenediazonium salt with the solution or suspension containing the resorcinol and/or its alkali metal salt or alkaline earth metal salt is addition of the alkaline mixture of the (substituted)benzenediazonium salt to the solution or suspension containing the resorcinol and/or its alkali metal salt or alkaline earth metal salt.

10. The production process as claimed in claim 9, wherein the addition of the alkaline mixture of the (substituted) benzenediazonium salt is dropwise addition, flowing down or pouring of the alkaline mixture of the (substituted) benzenediazonium salt.

11. The production process as claimed in claim 1, characterized in that the resorcinol and the (substituted) benzenediazonium salt are reacted in the presence of the alkali metal hydroxide or alkaline earth metal hydroxide 15 to 40 times by mol as much as the resorcinol.

12. The production process as claimed in claim 11, characterized in that the solution of the (substituted) benzenediazonium salt is added to the solution or suspension of a mixture of the resorcinol and its alkali metal hydroxide or alkaline earth metal hydroxide 15 to 40 times by mol as much as the resorcinol to conduct reaction.

13. The production process as claimed in claim 11, wherein the solvent is water or a mixture of water and a water-soluble organic solvent, and the amount of the resorcinol used is 2 to 20 wt % of the total amount of the reaction system.

14. The production process as claimed claim 11, wherein the (substituted)benzenediazonium salt of formula [1] is benzenediazonium chloride.

15. The production process as claimed in claim 11, wherein the solvent is water.

16. The production process as claimed in claim 11, wherein the hydroxide is sodium hydroxide or potassium hydroxid.

17. The production process as claimed in claim 12, wherein the addition of the solution of the (substituted) benzenediazonium salt is dropwise addition, flowing down or pouring of the (substituted)benzenediazonium salt.

* * * * *